United States Patent [19]

Coad

[11] 4,233,519
[45] Nov. 11, 1980

[54] RADIATION THERAPY APPARATUS HAVING RETRACTABLE BEAM STOPPER

[75] Inventor: George L. Coad, Lafayette, Calif.

[73] Assignee: Varian Associates, Inc., Palo Alto, Calif.

[21] Appl. No.: 49,837

[22] Filed: Jun. 18, 1979

[51] Int. Cl.³ .......................... G21F 5/04; G21K 1/02
[52] U.S. Cl. ...................................... 250/514; 250/522
[58] Field of Search .................. 250/522, 514, 492 R, 250/505, 521

[56] References Cited

U.S. PATENT DOCUMENTS 2,224,077  12/1940  Haupt et al. ......................... 250/514
2,412,662  12/1946  Watson ............................... 250/505

FOREIGN PATENT DOCUMENTS 557995  11/1957  Belgium .................................. 250/522

Primary Examiner—Alfred E. Smith
Assistant Examiner—T. N. Grigsby
Attorney, Agent, or Firm—Stanley Z. Cole; Leon F. Herbert

[57] ABSTRACT

A translation mechanism for linearly moving a beam stopper in radiation therapy apparatus includes first and second arms pivotally mounted to a support and third and fourth arms pivotally mounted to the first and second arms. The third and fourth arms are attached to the beam stopper and can comprise part of the beam stopper. In one embodiment, the third and fourth arms include disc shaped portions stacked in axial alignment with a drive motor attached to one disc portion ahd having a drive shaft axially aligned with and coupled to the other portion whereby relative rotation of the disc portions effects linear translation of the beam stopper.

20 Claims, 6 Drawing Figures

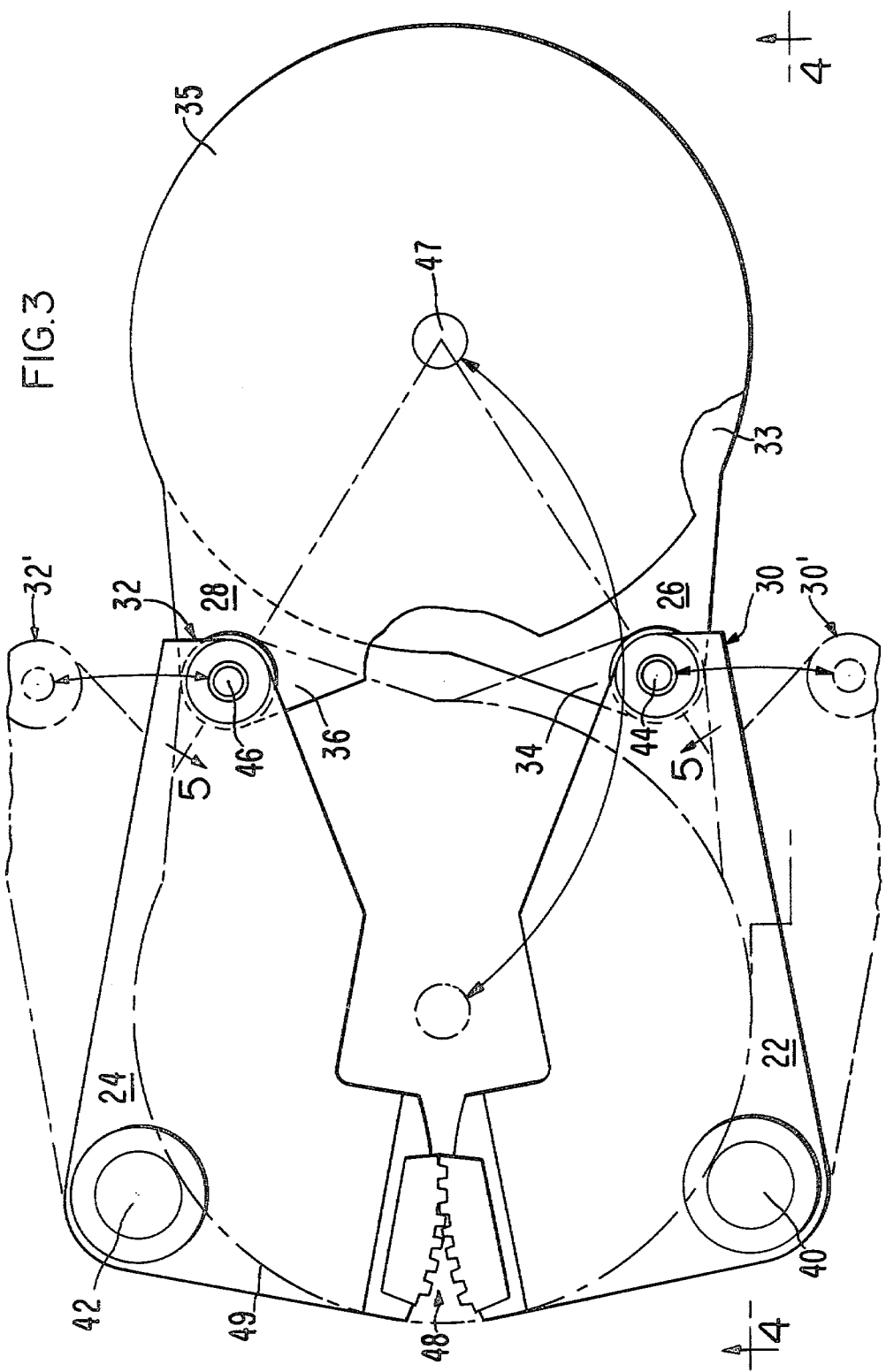

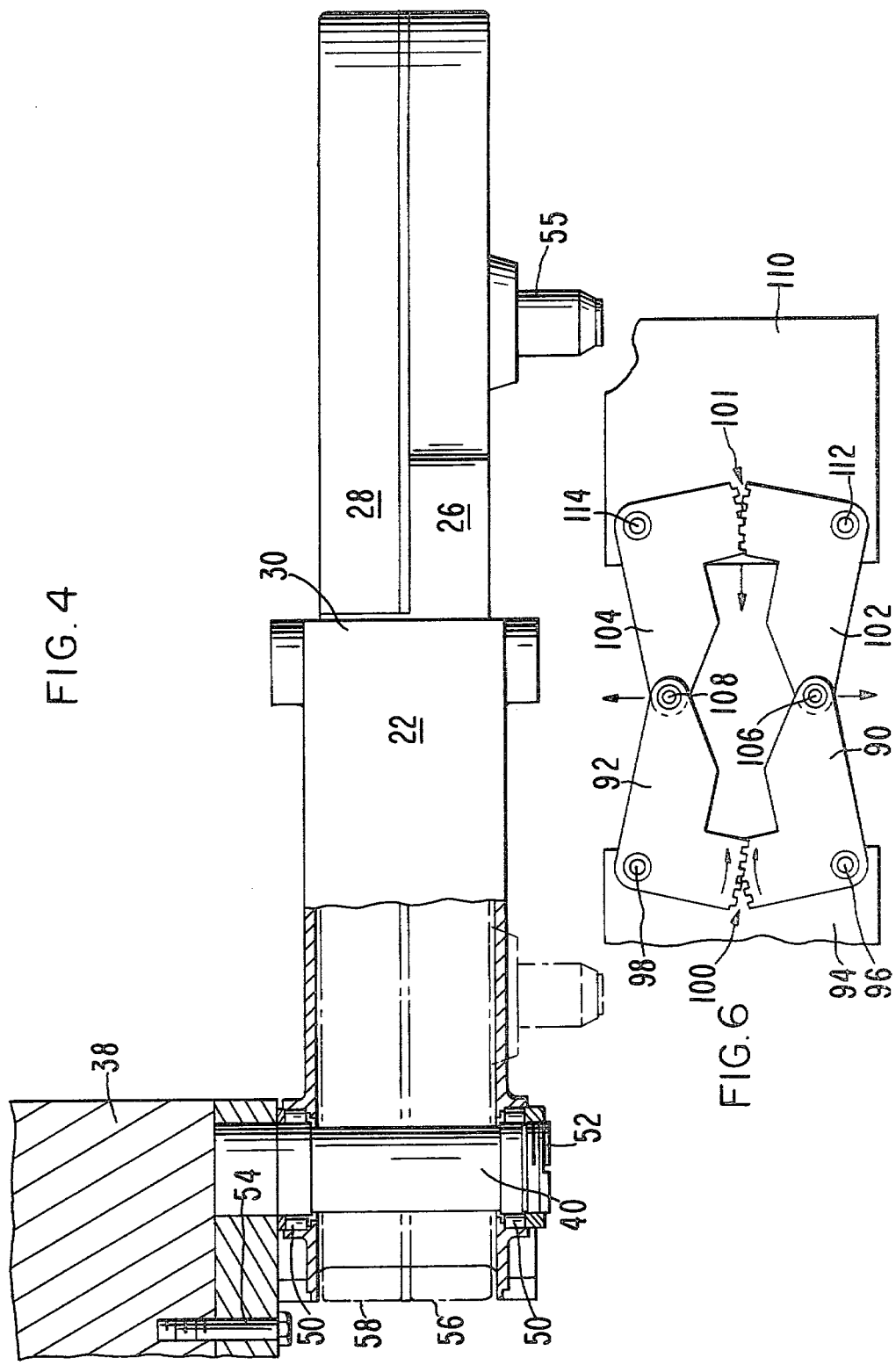

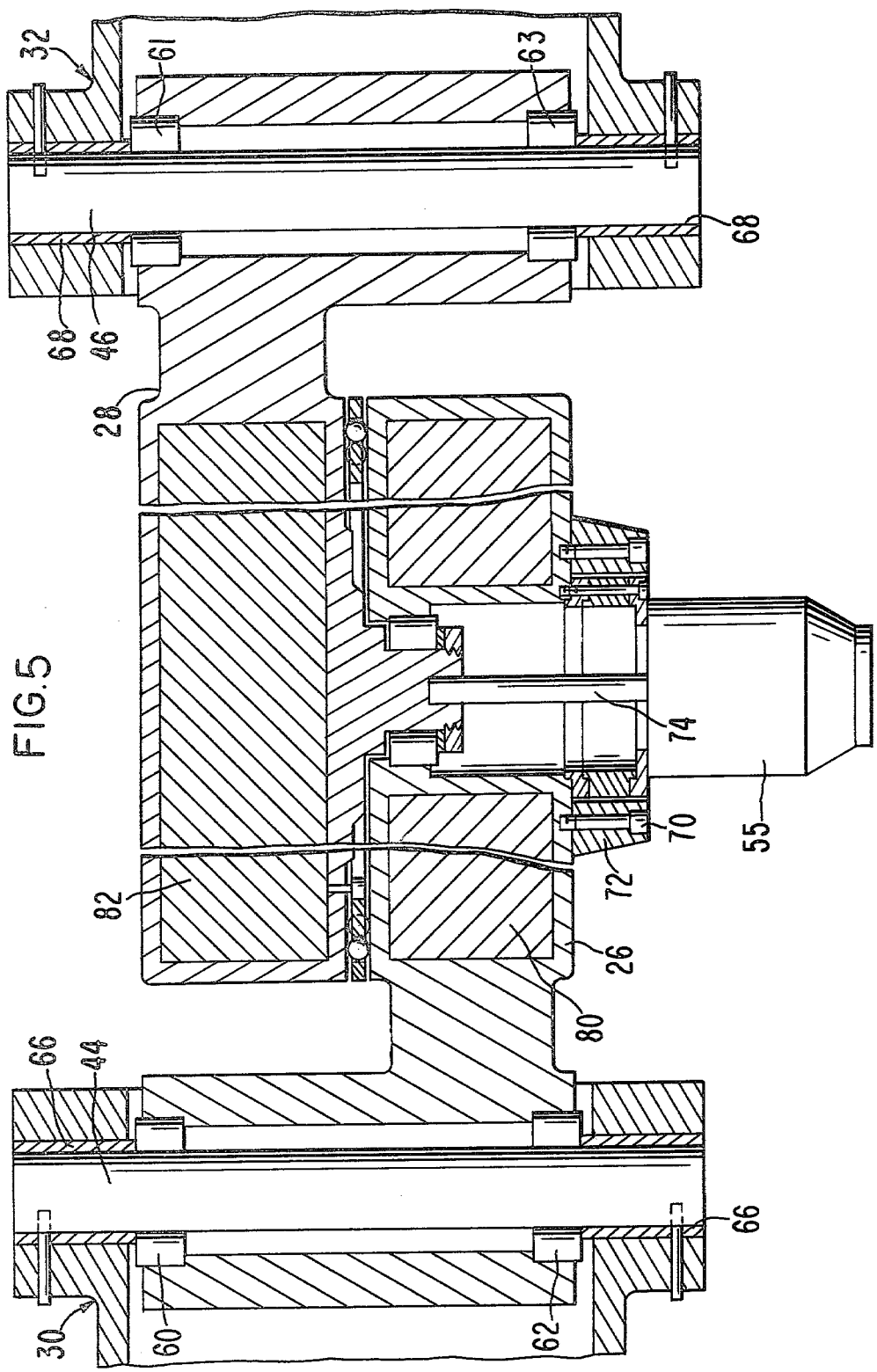

RADIATION THERAPY APPARATUS HAVING RETRACTABLE BEAM STOPPER

This invention relates generally to radiation therapy apparatus, and more particularly the invention relates to apparatus which utilizes a linear translation mechanism for positioning a beam stopper.

Radiation therapy apparatus typically includes a radiation source which is mounted to a support such as a C-shaped gantry for rotatable positioning of the source with respect to a target area such as a patient couch. Beam stopping means is provided on the gantry opposite from the radiation source for intercepting radiation passing through the target area.

The beam stopper typically comprises a large structure which can impede the work of a radiation therapist while a patient is being positioned in the target area prior to treatment. Attempts have been made at designing a retractable beam stopper by providing a sliding plate which can be removed from the target area when not in use. However, support means for a sliding beam stopper is unsatisfactory and the space required for accommodating the retracted structure is too great.

Accordingly, an object of the present invention is radiation therapy apparatus having a retractable beam stopper.

Another object of the invention is a beam stopper which can be retracted when not in use.

Still another of the invention is a retractable beam stopper which is readily accommodated in a retracted position.

A feature of the invention is a mechanism for linearly translating a structure in response to rotational drive means.

Briefly, radiation therapy apparatus in accordance with the present invention includes a radiation source, support means for rotating the radiation source about a target area, and beam stopper means retractably attached to the support means and positionable to receive radiation passing through the target area. The beam stopper means includes first and second arms rotatably attached to the support means and third and fourth arms which are pivotally attached to the first and second arms, respectively.

In one embodiment the third and fourth arms are pivotally attached to a beam stopper. Means is provided for mechanically coupling the first and second arms and the third and fourth arms whereby the coupled arms will pivot together. Drive means drives one of the coupled arms thereby causing the arms to rotate and the beam stopper to translate linearly.

In another embodiment the third and fourth arms comprise members of the beam stopper. Each of the members includes a generally disc shaped portion and a peripheral portion for attachment to an arm. The disc shaped portions are rotatably stacked in axial alignment, and drive means is attached to one of the members with the drive means having a drive shaft axially aligned with the disc shaped portions and mechanically coupled to the other of the members whereby the drive means effects relative rotation of the disc shaped portions. Means is provided for mechanically coupling the first and second arms whereby movement of the arms effects linear translation of the two members in response to the relative rotation of the two members. Alternatively, the drive means can be coupled to drive the first or second arm and thereby rotate and translate the stacked and axially coupled beam stopper members. Preferably, bearing means is provided between the two disc portions to facilitate the relative rotation thereof.

Thus, the linear translation mechanism in accordance with the invention effects linear movement of two members rotatably stacked in axial alignment in response to relative rotation of the two stacked members.

The invention and objects and features thereof will be more readily apparent from the following detailed description and appended claims when taken with the drawing.

In the drawings,

FIG. 3 is a plan view of radiation beam stopper apparatus in the radiation therapy machine of FIG. 2.

FIG. 4 is a side view partially in section of the beam stopper apparatus illustrated in FIG. 3.

FIG. 5 is a side view in section of the apparatus taken along the line 5—5 of FIG. 3.

FIG. 6 is a plan view of another embodiment of beam stopper apparatus in accordance with the invention.

Figure 1:
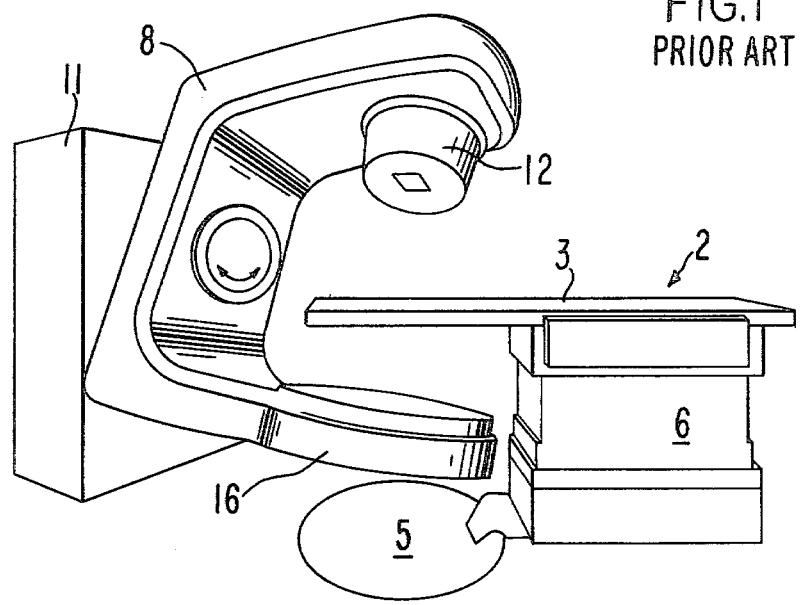
FIG. 1 is a perspective view of a conventional radiation therapy apparatus.

Referring now to the drawings, FIG. 1 is a perspective view of a conventional radiation therapy machine such as disclosed in U.S. Pat. No. 3,783,251, assigned to the present assignee. The machine includes a couch 2 having a table portion 3 which receives a patient to be treated. The couch is rotatable about a vertical axis by means of a turntable 5 to which the couch 2 is affixed.

A generally C-shaped gantry 8 is supported by a stand 11 and rotatable about a horizontal axis. A source of radiation, such as a linear accelerator producing a high energy electron beam which is directed against an X-ray target, produces a beam of X-rays emanating from a collimator head portion 12. The head portion 12 includes two sets of movable beam defining jaws, as of lead, which are movable to define the field of the X-ray beam.

The gantry 8 also includes a beam stopping portion 16 disposed along the X-ray beam axis and which holds an X-ray absorbing material, such as lead, for stopping and absorbing the X-ray beam. The beam stopper typically comprises a large structure to ensure reception of all radiation from the source, and since the beam stopper is normally permanently affixed to the gantry, the structure often interferes with a radiation therapist while a patient is being positioned in the target area prior to treatment.

In accordance with the present invention radiation therapy apparatus is provided with a retractable beam stopper which is readily accommodated in a retracted position and which is linearly translated to a beam stopping position for use during radiation treatment. The unique structure and drive mechanism permits the retractable beam stopper to be accommodated with radiation therapy apparatus in no more space than is required for conventional radiation therapy apparatus employing a fixed beam stopper.

The linear drive mechanism includes first and second arms which are pivotally mounted to a support structure and third and fourth arms which are pivotally mounted to ends of the first and second arms, respectively. In one embodiment, the third and fourth arms are pivotally mounted to a beam stopper with drive means provided to pivot the four arms and thereby move the beam stopper apparatus. Mechanical coupling means couples the arms whereby the coupled arms will simultaneously move and thereby effect linear translation of the beam stopper.

Alternatively, the third and fourth arms may comprise members of the beam stopper with the members pivotally coupled together. By mechanically coupling the first and second arms, the beam stopper apparatus is linearly translated in response to drive means. In one embodiment the beam stopper members may each include a generally disc shaped portion with the disc shaped portions stacked in axial alignment. The drive means is attached to one of the members with the drive means having a drive shaft axially aligned with the disc shaped portions and mechanically coupled to the other of the members whereby the drive means effects relative rotation of the disc shaped portions and thereby linearly translates the beam stopper as the first and second arms are pivoted.

Figure 2:
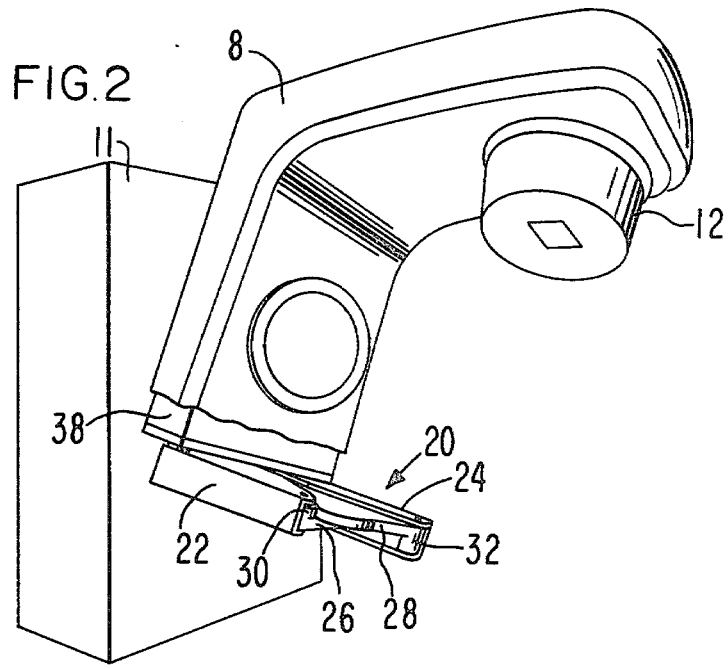
FIG. 2 is a perspective view of a radiation therapy machine in accordance with one embodiment of the present invention.

Illustrated in FIG. 2 is radiation therapy apparatus in accordance with one embodiment of the invention wherein the third and fourth arms comprising members of the beam stopper. Elements of the apparatus of FIG. 2 have the same reference numerals as like elements of the apparatus of FIG. 1. In this embodiment the retractable beam stopper shown generally at 20 is supportably mounted to the bottom portion of gantry 8 in a retracted position. The beam stopper includes two U-shaped support arms 22 and 24 and two beam stopper members 26 and 28 which are pivotally mounted at end portions 30 and 32 of arms 22 and 24, respectively. The other ends of arms 22 and 24 are pivotally mounted to the gantry 8. In the retracted position illustrated the members 26 and 28 are accommodated between and within the U-shaped arms 22 and 24.

A plan view of the retractable beam stopper apparatus 20 is illustrated in FIG. 3 with the beam stopper shown in an extended position and by dotted lines in the retracted position. Arms 22 and 24 are rotatably mounted to a support portion of the gantry by means of pivot pins 40 and 42, respectively. Members 26 and 28 are rotatably mounted to the end portions 30 and 32 of arms 22 and 24 by means of pivot pins 44 and 46, respectively.

Member 28 includes a generally disc shaped body portion 35 and a peripheral attachment portion 36 which is attached by pivot pin 46 to the end 32 of arm 24. Similarly, member 26 includes a generally disc shaped body portion 33 which is concentrically aligned with the disc shaped portion 35, as illustrated by the broken away portions of portion 35, and a peripheral attachment portion 34 which is joined by pivot pin 44 to the end portion 30 of arm 22. As will be described further hereinbelow, drive means is attached to member 26 with the drive means having a drive shaft axially aligned with the disc shaped portions of members 26 and 28 and mechanically coupled to member 28, as illustrated generally by the axially positioned circle 47. Thus, the drive means can effect relative rotation of the disc shaped portions of the two members 26, 28 which effects linear translation of the members.

In moving the beam stopper from the extended position to a retracted position within arms 22 and 24, as shown by dotted line, the disc portions of members 26 and 28 are rotated relative to each other thereby forcing arms 22 and 24 to rotate about pivot pins 40 and 42 with the end portions 30 and 32 of the arms moving outwardly to the positions 30' and 32', respectively. The arms 22 and 24 are mechanically coupled by means of the gear segments shown generally at 48 whereby rotation of one arm also causes rotation of the other arm. Thus, as the disc portions of the members 26 and 28 are rotated, the end portions of arms 22 and 24 move outwardly and the members 26 and 28 are linearly translated inwardly to the retracted position within arms 22 and 24, as shown by the dotted line 49.

FIG. 4 is a side view of the apparatus of FIG. 3 partially in section taken along the line 4—4 and illustrating the base and pin assembly for fastening arm 22 to the support frame 38. The base and pin assembly includes pivot pin 40 which extends through arm 22 with bearings 50 provided at either side of arm 22 to facilitate rotation thereof about pivot pin 40. Pivot pin 40 is locked in position in arm 22 by a fastener 52, and the base and pin assembly is fastened to support 38 by means of bolts 54.

Members 26 and 28 are shown in the extended position with a drive motor 55 mounted to the bottom of member 26. The retracted position of members 26 and 28 is illustrated by dotted lines 56 and 58, respectively, within arm 22.

Referring now to FIG. 5, a section view of the apparatus of FIG. 3 taken along the line 5—5 further illustrates the drive means for the disc portions of members 26 and 28 and the attachment of members 26 and 28 to the end portions 30 and 32, respectively, of the support arms. Portions of members 26 and 28 have been removed, as indicated by broken lines, to facilitate the illustration. Cavities 80 and 82 in members 26 and 28 are filled with radiation absorbing material, such as lead.

The peripheral portion of member 26 is rotatably attached to the end portion 30 of arm 22 by means of pivot pin 44 and thrust collars 66. Bearings 60 and 62 facilitate rotation of member 26. Similarly, member 28 is rotatably supported by bearings 61 and 63 on pivot pin 46 which is positioned within thrust collars 68 within end portion 32 of arm 24.

Motor 55 is mounted by bolts 70 and lead collar 72 to member 26, and shaft 74 is attached to the driven member 28. The drive means is preferably a low speed electric motor such as a Bodine 42D3 DEPM motor, and a drive transmission. Thus, when motor 55 is energized member 28 is driven in relative rotation with respect to member 26 with the rotating members pivoting about the pivot pins 44 and 46 and rotating the end portions 30 and 32 of arms 22 and 24, as illustrated in FIG. 3. The direction of lateral translation of members 26 and 28 depends on the direction of rotation of motor 55. Bearings 84 and 86 are provided between members 26 and 28 to facilitate the relative rotation thereof.

FIG. 6 is a plan view of another embodiment of the invention in which the linear translation mechanism includes first and second arms 90 and 92 which are pivotally mounted to the gantry 94 at portions 96 and 98, respectively. Again, in this embodiment the arms 90 and 92 are mechanically coupled by the gear segments shown generally at 100, and arms 102 and 104 are mechanically coupled by the gear segments shown generally at 101. Drive means such as a motor is coupled to arm 90 at pivot point 96 to drive the mechanism.

Arms 102 and 104 are pivotally attached to arms 90 and 92 at end portions 106 and 108, respectively. The other ends of arms 102 and 104 are attached to beam stopper 110 by pivot pins 112 and 114, respective. The arms can be attached to beam stopper 110 by other suitable means such as with cam followers attached to the periphery of the beam stopper.

In this embodiment, the drive motor rotates arms 90 and 92 which are coupled by gear segment 100, and end portions 106 and 108 move outwardly, as indicated by the arrows. Consequently, beam stopper 110 moves inwardly towards the gantry 94, as indicated by the arrow. Reverse rotation of the drive motor moves the beam stopper 110 in the opposite direction to an extended position.

It will be appreciated that this embodiment can be readily modified with the drive motor driving either arm 102 or 104. The drive motor could then be mounted to the beam stopper 110. Atlernatively, cylinder drive means can be mounted on one arm and attached to translate an opposing arm, or cylinder drive means can be mounted to the support and attached to translate the beam stopper.

The linear translation mechanism in accordance with the present invention has proved to be particularly advantageous in a radiation therapy machine for efficiently extending and retracting a large beam stopper structure, thus facilitating unimpeded movement of a therapist about the machine before or after the actual radiation therapy. The mechanism can be employed without requiring additional space for the radiation therapy machine.

While the invention has been described with reference to specific embodiments and applications, the description is illustrative of the invention and is not to be construed as limiting the invention. Thus, it will be appreciated that various modifications and applications may occur to those skilled in the art without departing from the true spirit and scope of the invention as defined by the appended claims.

What is claimed is:

1. Radiation therapy apparatus comprising a radiation source, support means for rotating said radiation source about a target area, beam stopper means retractably attached to said support means and positionable to receive radiation passing through the target area, said beam stopper means including first and second arms pivotally attached to said support means, third and fourth arms pivotally attached to said first and second arms, respectively, a beam stopper, means for attaching said third and fourth arms to said beam stopper, and drive means coupled to one of said arms whereby said arms rotate and said beam stopper translates linearly.

2. Radiation therapy apparatus as defined by claim 1 and including means for mechanically coupling at least two arms whereby rotation of one arm rotates the other arm.

3. Radiation therapy apparatus as defined by claim 2 wherein said mechanical coupling means comprises gear means.

4. Radiation therapy apparatus as defined by claim 1 wherein said third and fourth arms comprise part of said beam stopper.

5. Radiation therapy apparatus as defined by claim 4 wherein said third and fourth arms include generally disc shaped portions and said disc shaped portions are stacked in axial alignment and rotatable about said axis.

6. Radiation therapy apparatus as defined by claim 5 wherein said drive means coupled to one of said arms includes a drive motor attached to one of said disc shaped portions with a drive shaft axially aligned with and coupled to the other disc shaped portion.

7. Radiation therapy apparatus comprising a radiation source, support means for rotating said radiation source about a target area, beam stopper means retractably attached to said support means and positionable to receive radiation passing through the target area, said beam stopper means including first and second arms pivotally attached to said support means, first and second members, each of said first and second members including a generally disc shaped portion and a peripheral attachment portion, means for rotatably attaching said peripheral attachment portions of said first and second members to said first and second arms, respectively, said disc shaped portions being rotatably stacked in axial alignment, drive means for pivoting said arms and rotating said members whereby said members are translated linearly.

8. Radiation therapy apparatus as defined by claim 7 wherein said drive means is coupled to and drives one of said arms.

9. Radiation therapy apparatus as defined by claim 7 wherein said drive means is attached to one of said members and has a drive shaft axially aligned with said disc shaped portions and coupled to the other of said members whereby said drive means effects relative rotation of said disc shaped portions and said arms effect linear translation of said members in response to said relative rotation.

10. Radiation therapy apparatus as defined by claim 7 and further including means for mechanically coupling said first and second arms whereby rotation of one arm relative to said support means rotates the other arm relative to said support means.

11. Radiation therapy apparatus as defined by claim 10 wherein said mechanical coupling means comprises gear means.

12. Radiation therapy apparatus as defined by claim 11 wherein said gear means includes a first gear sector mounted to said first arm and a second gear sector mounted to said second arm, whereby said first and second gear sectors engage each other as said arms rotate.

13. Radiation therapy apparatus as defined by claim 7 further including bearing means between said disc portions to facilitate relative rotation thereof.

14. For use with a radiation therapy machine and the like, a retractable beam stopper comprising first and second members, each member including a generally disc shaped portion and a peripheral attachment portion, said disc shaped portions being rotatably stacked in axial alignment, first and second arms, means for pivotally attaching end portions of each of said first and second arms to a peripheral attachment portion of each of said first and second members, respectively, means for pivotally attaching another end of each arm to support means, means mechanically coupling said first and second arms whereby pivoting one arm relative to said support means pivots the other arm relative to said support means, and drive means for pivoting said arms and rotating said disc shaped portions thereby linearly translating said beam stopper.

15. A retractable beam stopper as defined by claim 14 wherein said drive means is coupled to one of said arms.

16. A retractable beam stopper as defined by claim 14 wherein said drive means is attached to one of said members and has a drive shaft axially aligned with said disc shaped portions and is mechanically coupled to the other of said members.

17. A retractable beam stopper as defined by claim 16 wherein said drive means effects relative rotation of said disc portions and said arms effect linear translation of said members in response to said relative rotation.

18. A retractable beam stopper as defined by claim 17 and further including bearing means between said disc shaped portions to facilitate relative rotation thereof.

19. A retractable beam stopper as defined by claim 14 wherein said mechanical coupling means comprises gear means.

20. A retractable beam stopper as defined by claim 19 wherein said gear means comprises a first gear sector mounted to said first arms, a second gear sector mounted to said second arms, said first and second gear sectors engaging each other as said arms are rotated.

* * * * *